(12) United States Patent
Amedee et al.

(10) Patent No.: US 10,143,774 B2
(45) Date of Patent: Dec. 4, 2018

(54) POROUS POLYSACCHARIDE SCAFFOLD COMPRISING NANO-HYDROXYAPATITE AND USE FOR BONE FORMATION

(71) Applicants: Joelle Amedee, Bordeaux (FR); Didier Letourneur, Paris (FR); Catherine Le Visage, Paris (FR); Sidi Mohammed Derkaoui, Paris (FR); Jean-Christophe Fricain, Bordeaux (FR); Sylvain Catros, Bordeaux (FR)

(72) Inventors: Joelle Amedee, Bordeaux (FR); Didier Letourneur, Paris (FR); Catherine Le Visage, Paris (FR); Sidi Mohammed Derkaoui, Paris (FR); Jean-Christophe Fricain, Bordeaux (FR); Sylvain Catros, Bordeaux (FR)

(73) Assignees: INSERM (INSTITUT NATIONAL DE LA SANTÉ ET DE LA RECHERCHE MÉDICALE), Paris (FR); UNIVERSITE DE BORDEAUX II VICTOR SEGALEN, Bordeaux (FR); UNIVERSITÉ PARIS DIDEROT—PARIS 7, Paris (FR)

( * ) Notice: Subject to any disclaimer, the term of this patent is extended or adjusted under 35 U.S.C. 154(b) by 0 days.

(21) Appl. No.: 15/657,868

(22) Filed: Jul. 24, 2017

(65) Prior Publication Data
US 2017/0319741 A1    Nov. 9, 2017

Related U.S. Application Data

(62) Division of application No. 14/728,412, filed on Jun. 2, 2015, now Pat. No. 9,757,494, which is a division of application No. 13/819,546, filed as application No. PCT/EP2011/064924 on Aug. 30, 2011, now abandoned.

(30) Foreign Application Priority Data

Aug. 31, 2010   (EP) .................................... 10305932

(51) Int. Cl.
| | | |
|---|---|---|
| *A61L 27/20* | (2006.01) | |
| *A61L 27/12* | (2006.01) | |
| *A61L 27/56* | (2006.01) | |
| *A61L 27/46* | (2006.01) | |
| *C08B 37/00* | (2006.01) | |
| *C08B 37/02* | (2006.01) | |
| *C08J 9/00* | (2006.01) | |
| *C08J 9/26* | (2006.01) | |
| *C08J 9/28* | (2006.01) | |

(52) U.S. Cl.
CPC .............. *A61L 27/12* (2013.01); *A61L 27/20* (2013.01); *A61L 27/46* (2013.01); *A61L 27/56* (2013.01); *C08B 37/0018* (2013.01); *C08B 37/0021* (2013.01); *C08J 9/0061* (2013.01); *C08J 9/26* (2013.01); *C08J 9/28* (2013.01); *A61L 2300/112* (2013.01); *A61L 2400/08* (2013.01); *A61L 2400/12* (2013.01); *A61L 2430/02* (2013.01); *C08J 2201/026* (2013.01); *C08J 2201/0444* (2013.01); *C08J 2201/0484* (2013.01); *C08J 2205/022* (2013.01); *C08J 2207/10* (2013.01); *C08J 2305/00* (2013.01); *C08J 2405/02* (2013.01)

(58) Field of Classification Search
None
See application file for complete search history.

(56) References Cited

U.S. PATENT DOCUMENTS

| | | | |
|---|---|---|---|
| 9,555,164 B2 * | 1/2017 | Le Visage | ............... A61L 27/20 |
| 2003/0180344 A1 | 9/2003 | Wise et al. | |
| 2006/0153814 A1 | 7/2006 | Liao et al. | |
| 2010/0221303 A1 | 9/2010 | Le Visage et al. | |
| 2017/0080123 A1 * | 3/2017 | Le Visage | ............... A61L 27/20 |

FOREIGN PATENT DOCUMENTS

| | | |
|---|---|---|
| WO | 2009/047346 A1 | 4/2009 |
| WO | 2009/047347 A1 | 4/2009 |

OTHER PUBLICATIONS

Liuyun et al., "Preparation and properties of a novel bone repair composite: nano HAP/chitosan/CMC", J. Mater Sci: Mat Med, Jan. 1, 2008, pp. 981-987, vol. 19.
Kong et al., "Preparation and characterization of nano-hydroxyapatite/chitosan composite scaffolds", J. Biomed Mat Res, Nov. 1, 2005, pp. 275-282, vol. 75A, No. 2.
Li et al., "Preparation and in vitro investigation of chitosan/nano-hydroxyapatite composite used as bone substitute materials", J. Mater Sci: Mat Med, 2005, pp. 213-219, vol. 16.
Jiang Liuyun et al: "Preparation and biological properties of a novel composite scaffold of nano-hydroxyapatite/chitosan/carboxymethyl cellulose for bone tissue engineering", Journal of Biomedical Science, 15:65, Jul. 14, 2009.
R. Murugan et al: "Bioresorbable composite bone paste using polysaccharide based on nano hydroxyapatite", Biomaterials 25, pp. 3829-3835, Oct. 7, 2003.
W. W. Thien-Han et al: "Biomimetic chitosan-nanohydroxyapatite composite scaffolds for bone tissue engineering", Acta Biomaterialia, pp. 1182-1197, Dec. 10, 2008.

* cited by examiner

*Primary Examiner* — Abigail Vanhorn
(74) *Attorney, Agent, or Firm* — W&C IP

(57) ABSTRACT

The present invention relate to three dimensional porous polysaccharide matrices able to induce mineralization of a tissue in osseous site, as well as in non-osseous site, in the absence of stem cells or growth factors.

18 Claims, 9 Drawing Sheets

A : Matrix + n-HA (MATRI+)

B : Matrix without n-HA

A

B

Figure 1:
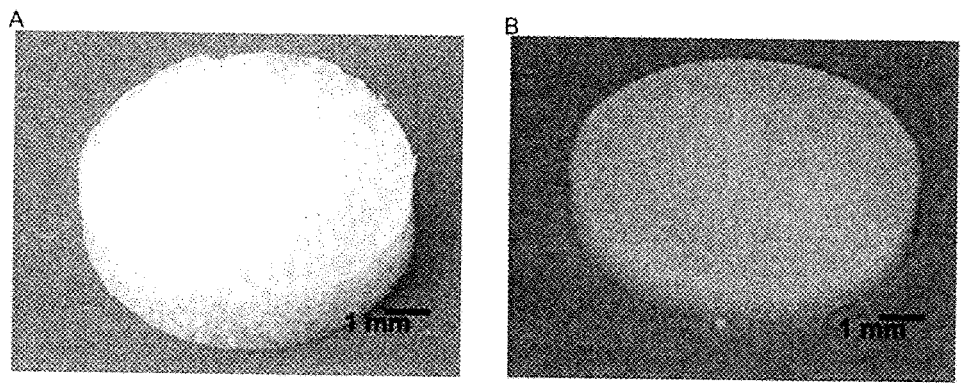

POROUS POLYSACCHARIDE SCAFFOLD COMPRISING NANO-HYDROXYAPATITE AND USE FOR BONE FORMATION

CROSS-REFERENCE TO RELATED APPLICATIONS

This application is a divisional application of U.S. Ser. No. 14/728,412 filed Jun. 2, 2015, now U.S. Pat. No. 9,757,494, which was a divisional of U.S. Ser. No. 13/819, 546, filed May 9, 2013, which was a Rule 371 national stage filing from PCT/EP2011/064924 filed Aug. 30, 2011, which claimed priority to European Application 10305932.5 filed Aug. 31, 2010.

FIELD OF THE INVENTION

The present invention relates to a method for preparing a porous polysaccharide scaffold comprising hydroxyapatite, preferably nano-hydroxyapatite, that supports mineralization of tissues. The present invention further provides a porous polysaccharide scaffold obtainable by said method, and its use for bone formation.

BACKGROUND OF THE INVENTION

The topic of bone-related disorders has gained considerable attention over the past years. The use of autologous and allograft bones has been popularly implemented in clinics for overcoming bone related disorders, such as bone defect. However, the use of autologous bone is known to result in secondary trauma and allograft bone induces immune repulsion. In addition, autologous and allograft bones present serious limitations since their uses are dependent on the size and the localisation of the defect. For example, it was reported that grafts in large defects were resorbed by the body before the completion of osteogenesis, which leaves a doubt about the success of this therapy (Hoexter D L. *Bone regeneration graft materials* J Oral Implantol. 2002; 28(6); Delloye C, Cornu O, Druez V, Barbier O. *Bone allografts: What they can offer and what they cannot*. J Bone Joint Surg Br. 2007 May; 89(5):574-9).

To remedy to those drawbacks, many works have focus their interest into replacing natural bone by synthetically prepared implants, capable of inducing mineralisation and of supporting new bone formation. Three dimensional scaffolds have thus been explored to repair tissues that do not self develop spontaneously. Thus, scaffold-based tissues engineering has become a promising strategy in regenerative medicine, because cells alone lack the ability to form three dimensional tissues without the support of an artificial structure.

Prior art discloses porous scaffolds suitable for tissue engineering since their porous structure promotes cell colonization and tissue formation within the scaffold.

However, using said scaffolds for the treatment of bone related disorders still present various drawbacks related to the disease to be treated, as it depends on the type, size, and localisation of the damaged bone, as well as on the nature, age and sex of the subject to be treated.

Currently, many works are based on the use of bioactive and biocompatible material such as hydroxypatite. Indeed, hydroxyapatite, which is able to bond with the bone, is used as a filler to replace amputated bone or as a coating to promote bone ingrowth into prosthetic implants. However, the use of hydroxypatite presents limitations since it is mainly effective on osseous sites.

There is currently no available technique providing bone formation which does not present any risk of rejection and which may be independent of the size and localisation of the bone to regenerate.

Consequently, there is a need for a biocompatible porous material, which can be used on any subject, independently of the type, size and localisation of the damaged bone, and is capable of promoting bone formation and providing osteoinductive properties.

SUMMARY OF THE INVENTION

The inventors have prepared porous three-dimensional polysaccharide scaffold able to provide an ideal environment for bone formation and facilitate the growth of vasculature into the material. Surprisingly and unexpectedly, the inventors have shown that polysaccharide scaffold comprising nanocristalline hydroxyapatite induce mineralisation of a tissue. Thus, by stimulating undifferentiated cells in situ into bone cell lineages, the invention overcomes the limitations of the prior art strategies of treatment of bone related disorders.

The inventors have thus found out very promising polysaccharide scaffolds for bone formation, in a non-osseous site, in the absence of growth factors or stem cells. The invention hence challenges the currently acknowledged techniques for treating bone related disorders and offers a wide range of possibilities disclosed hereafter.

The invention relates to a method for preparing a porous polysaccharide scaffold comprising the following step:

i) preparing an alkaline aqueous solution comprising an amount of at least one polysaccharide, an amount of a cross-linking agent and an amount of a porogen agent, ii) transforming the solution into a hydrogel by placing said solution at a temperature from about 4° C. to about 80° C. for a sufficient time to allow the cross-linking of said amount of polysaccharide, iii) submerging said hydrogel into a solvent, preferably an aqueous solution, and iv) washing the porous polysaccharide scaffold obtained at step iii), wherein the alkaline aqueous solution of step i) further comprises hydroxyapatite, preferably nano-hydroxyapatite.

The invention also relates to a method for preparing a porous polysaccharide scaffold comprising the following steps:

a) preparing an alkaline aqueous solution comprising an amount of at least one polysaccharide and one cross-linking agent, b) freezing the aqueous solution of step a), c) sublimating the frozen solution of step b), wherein the alkaline aqueous solution of step a) further comprises hydroxyapatite, preferably nano-hydroxyapatite, and wherein step b) is performed before the cross-linking of the polysaccharide occurs in the solution of step a).

The invention further relates to a porous polysaccharide scaffold obtainable by the method of the invention.

The invention further relates to a porous polysaccharide scaffold obtainable according to the method of the invention, for use in the treatment of bone related disorders.

DETAILED DESCRIPTION OF THE INVENTION

Definition

As used herein, the term "polysaccharide" refers to a molecule comprising two or more monosaccharide units.

As used herein, the term "alkaline solution" refers to a solution having a pH strictly superior to 7.

As used herein, the term "aqueous solution" refers to a solution in which the solvent is water.

As used herein, the term "porogen agent" refers to any solid agent which has the ability to form pores within a solid structure.

As used herein, the term "cross-linking" refers to the linking of one polysaccharide chain to another one with covalent bonds.

As used herein, the term "cross-linking agent" encompasses any agent able to introduce cross-links between the chains of the polysaccharides of the invention.

As used herein, the term "scaffold" or "matrix" refers to a semi-solid system comprising a three-dimensional network of one or more species of polysaccharide chains. Depending on the properties of the polysaccharide (or mixtures of polysaccharides) used, as well as on the nature and density of the network, such structures in equilibrium can comprise various amounts of water. In the following, the terms "scaffold" and "matrix" are interchangeable.

As used herein, the term 'hydroxyapatite', or "microhydroxyapatite" or "HA" refers to a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. The $OH^-$ ion can be replaced by fluoride, chloride or carbonate, producing fluorapatite or chlorapatite. Preferably, for the purpose of the invention, the $OH^-$ is not replaced. Hydoxyapatite is the major component of bone and teeth matrix and gives bones and teeth their rigidity. Typically, the size of the microparticles of hydroxyapatite is comprised between 1 to 20 µm, preferably 5 and 15 µm.

As used herein, the term "nanocristalline hydroxyapatite", or "nano-hydroxyapatite", or "n-HA", refers to hydroxyapatite crystal particles having a size comprised between 10 and 100 nm, preferably 20 and 80 nm, preferably 30 and 70 nm, preferably between 30 and 60 nm, and most preferably about 50 nm. Preferably, the n-HA particles are needle-shaped. Preferably, the n-HA suitable for carrying out the present invention is a n-HA prepared by chemical precipitation at room temperature, for example by precipitation of a solution of phosphoric acid with a solution of calcium hydroxide.

As used herein, the term "porous composite polysaccharide scaffold" refers to a porous scaffold comprising polysaccharides associated with n-HA according to the invention.

As used herein, the term "biodegradable" refers to materials that degrade in vivo to non-toxic compounds, which can be excreted or further metabolized.

As used herein, the term "sublimation" refers to the physical phase transition from a solid state directly to a vapor state. More specifically, sublimation is a process in which a substance goes from a solid to a gas without going through a liquid phase. Sublimation of a solution may be obtained through the freeze-drying process.

As used herein, the term "freeze-drying" refers the drying of a deep-frozen material under high vacuum by freezing out the solvent (ie. water) and then evaporating it in the frozen state.

As used herein, the terms "treating", "treatment" and "therapy" refer to therapeutic treatment and prophylactic, or preventative manipulations, or manipulations which stimulate bone cell differentiation or bone formation. Such expression also encompasses manipulations which postpone the development of bone disorder symptoms, and/or reduce the severity of bone disorders and/or such symptoms that will or are expected to develop from a bone disorder. The terms further include ameliorating existing bone disorder symptoms, preventing additional symptoms, or preventing or promoting bone growth.

As used herein, the expression "bone tissue" refers to calcified tissues (e.g., calvariae, tibiae, femurs, vertebrae, teeth), bone trabeculae, the bone marrow cavity, the cortical bone, which covers the outer peripheries of the bone trabeculae and the bone marrow cavity, and the like. The expression "bone tissue" also encompasses bone cells that are generally located within a matrix of mineralized collagen; blood vessels that provide nutrition for the bone cells; bone marrow aspirates: joint fluids: bone cells that are derived from bone tissues; and may include fatty bone marrow. Finally, bone tissue includes bone products such as whole bones, sections of whole bone, bone chips, bone powder, bone tissue biopsy, collagen preparations, or mixtures thereof. For the purposes of the present invention, the term "bone tissue" is used to encompass all of the aforementioned bone tissues and products, whether human or animal, unless stated otherwise.

As used herein, the expression "bone-related disorders" includes disorders of bone formation and bone resorption. Preferably, the expression "bone related disorders" refers to diseases associated with insufficiency of bone formation or bone loss.

Non-limiting examples of bone related disorders are rickets, osteoporosis osteomalacia, osteopenia, bone cancer, arthritis, rickets, bone fracture, bone defects, osteolytic bone disease, osteomalacia, bone frailty, loss of bone mineral density achondroplasia, cleidocranial dysostosis, Paget's disease, osteogenesis imperfecta, osteopetrosis, sclerotic lesions, pseudoarthrosis, periodontal disease, anti-epileptic drug induced bone loss, weightlessness induced bone loss, postmenopausal bone loss, osteoarthritis, infiltrative disorders of bone, metabolic bone diseases, organ transplant related bone loss, adolescent idiopathic scoliosis, glucocorticoid-induced bone loss, heparin-induced bone loss, bone marrow disorders, malnutrition, calcium deficiency, rheumatoid arthritis, hypogonadism, HIV associated bone loss, tumor-induced bone loss, cancer-related bone loss, hormone ablative bone loss, multiple myeloma drug-induced bone loss, facial bone loss associated with aging, cranial bone loss associated with aging, jaw bone loss associated with aging, skull bone loss associated with aging, and bone loss associated with space travel.

Preferably, the bone related disorders, as used herein, are bone fracture, large bone defects, rickets, osteoporosis, osteogenesis imperfecta, osteomalacia, osteopenia, bone cancer, osteolytic bone disease, bone frailty and/or loss of bone mineral density.

Porous Polysaccharide Scaffolds and Methods for Preparing Thereof

In a first object, the invention relates to a method for preparing a porous polysaccharide scaffold comprising the following step:

i) preparing an alkaline aqueous solution comprising an amount of at least one polysaccharide, an amount of a cross-linking agent and an amount of a porogen agent, ii) transforming the solution into a hydrogel by placing said solution at a temperature from about 4° C. to about 80° C. for a sufficient time to allow the cross-linking of said amount of polysaccharide, iii) submerging said hydrogel into a solvent, preferably an aqueous solution, and iv) washing the porous polysaccharide scaffold obtained at step iii), wherein the alkaline aqueous solution of step i) further comprises hydroxyapatite, preferably nano-hydroxyapatite.

The concentration of the porogen agent affects both the total porosity and the size of the pores formed in the scaffolds, so that the porosity and the pore size can be under the control of the concentration of said porogen agent.

Non-limiting examples of porogen agents are sodium chloride, calcium chloride, ammonium carbonate, ammonium bicarbonate, calcium carbonate, sodium carbonate, and sodium bicarbonate and mixtures thereof. Many of these compounds are available commercially from companies such as Sigma-Aldrich (St. Louis, Mich., US).

Preferably, in the context of the present invention, the porogen agent is chosen from sodium chloride, calcium chloride or mixtures thereof.

Alternatively, the porogen agent may be an inorganic salt that can be dissolved once the cross-linked polysaccharide scaffold is immersed in water. An example of such a porogen agent includes saturated salt solution, which would be dissolved progressively.

Typically, the weight ratio of the polysaccharide to the porogen agent is in a range 1:50 to 50:1, preferably from 1:30 to 30:1, preferably from 1:12 to 12:1. In a preferred embodiment, said weight ratio of the polysaccharide to the porogen agent is about 12:14.

Typically, the aqueous solution of step iii) is water.

Alternatively, the aqueous solution of step iii) is a buffer solution. Non-limiting examples of buffer solution are PBS (Phosphate buffered saline), EDTA (ethylenediaminetetraacetic acid), TAPS (3-{[tris(hydroxymethyl)methyl] amino} propanesulfonic acid), Bicine (N,N-bis(2-hydroxyethyl)glycine), Tris (tris(hydroxymethyl)methylamine), Tricine (N-tris(hydroxymethyl)methylglycine), HEPES (4-2-hydroxyethyl-1-piperazineethanesulfonic acid), MOPS (3-(N-morpholino)propanesulfonic acid), PIPES (piperazine-N,N'-bis(2-ethanesulfonic acid), Cacodylate (dimethylarsinic acid), SSC (saline sodium citrate), MES (2-(N-morpholino)ethanesulfonic acid) and mixtures thereof.

Alternatively, the aqueous solution of step iii) is an acidic solution. The acid may be selected from the group consisting of citric acid, hydrochloric acid, acetic acid, formic acid, tartaric acid, salicylic acid, benzoic acid, and glutamic acid.

Preferably, the aqueous solution of step iii) is a buffer solution. Most preferably, the aqueous solution of step iii) is phosphate buffer saline (PBS).

Preferably, the solvent of step ii) is an inorganic solvent.

In one embodiment, the method of the invention may comprise a further step, consisting of freeze-drying the scaffold obtained at step iv). Freeze-drying may be performed with any apparatus known in the art. There are essentially three categories of freeze dryers: rotary evaporators, manifold freeze dryers, and tray freeze dryers. Such apparatus are well known in the art and are commercially available such as a freeze-dryer Lyovac (GT2, STERIS Rotary vane pump, BOC EDWARDS). Basically, the vacuum of the chamber is from 0.1 mBar to about 6.5 mBar. The freeze-drying is performed for a sufficient time sufficient to remove at least 98.5 of the water, preferably at least 99% of the water, more preferably at least 99.5%.

In another embodiment, the method of the invention may comprise a further step consisting of hydrating the scaffold as prepared according to the invention. Said hydration may be performed by submerging the scaffold in an aqueous solution (e.g., de-ionized water, water filtered via reverse osmosis, a saline solution, or an aqueous solution containing a suitable active ingredient) for an amount of time sufficient to produce a scaffold having the desired water content. Typically, when a scaffold comprising the maximum water content is desired, the scaffold is submerged in the aqueous solution for an amount of time sufficient to allow the scaffold to swell to its maximum size or volume. Typically, the scaffold is submerged in the aqueous solution for at least about 1 hour, preferably at least about 2 hours, and more preferably about 4 hours to about 24 hours. It is understood that the amount of time necessary to hydrate the scaffold to the desired level will depend upon several factors, such as the composition of the used polysaccharides, the size (e.g., thickness) of the scaffold, and the temperature of the aqueous solution, as well as other factors.

Preferably, the hydrated scaffold comprises more than 80% of water, preferably 90% of water, most preferably 95% of water.

In a second aspect, the invention relates to a method for preparing a porous polysaccharide scaffold comprising the following steps:
a) preparing an alkaline aqueous solution comprising an amount of at least one polysaccharide, and one cross-linking agent,
b) freezing the aqueous solution of step a),
c) sublimating the frozen solution of step b), wherein the alkaline aqueous solution of step a) further comprises hydroxyapatite, preferably nano-hydroxyapatite,
and wherein step b) is performed before the cross-linking of the polysaccharide occurs in the solution of step a).

It is an essential feature of the invention that step b) is performed before the cross-linking of the polysaccharide occurs in the solution of step a). Typically, temperature and time are the main factors to control the cross-linking of the aqueous solution. To avoid or to seriously limit the cross-linking of the polysaccharide, the aqueous solution may be prepared at a temperature under 37° C., more preferably comprised between 4° C. and 25° C. Moreover, the step b) may be performed as quickly as possible to avoid the cross-linking of said polysaccharide.

Once the aqueous solution is prepared, it is frozen. The freezing of the aqueous solution may be performed at different rates (e.g., ° C./min). Typically, the freezing may be performed at rate from about 1° C./min to about 200° C./min, preferably from about 1° C./min to about 20° C./min, and most preferably from about 5° C./min to about 10° C./min. The solution may be frozen in liquid nitrogen or in dried ice.

When the aqueous solution is frozen, sublimation may take place. In a preferred embodiment, the method for preparing porous polysaccharide scaffolds according to the present invention includes a freeze-drying process. Therefore, according to the invention, the freeze-drying process has to take place before the cross-linking process occurs in the aqueous solution. Freeze-drying may be performed with any apparatus known in the art. There are essentially three categories of freeze dryers: rotary evaporators, manifold freeze dryers, and tray freeze dryers. Such apparatus are well known in the art and are commercially available such as a freeze-dryer Lyovac (GT2, STERIS Rotary vane pump, BOC EDWARDS). Basically, the deep-frozen aqueous solution is placed in a chamber. Then the chamber temperature is increased to a level higher than the boiling point of the liquefied vapour, whereby the vapour is vaporized and removed. Typically, the temperature of chamber may be from −70° C. to −1° C., preferably from −70° C. to −40° C., further preferably about −50° C. to −40° C. The heating of the chamber is accompanied with a vacuum flow to decrease the pressure of the chamber. Typically, the vacuum of the chamber is from 0.1 mBar to about 6.5 mBar. Typically, the freeze-drying is performed for a sufficient time sufficient to remove at least 98.5% of the water, preferably at least 99% of the water, more preferably at least 99.5%.

The freezing of the aqueous solution causes the formation of ice particles from the water. Without to be bound by any theory, under the temperature and pressure condition described above, water included in the frozen solution is sublimed, and thus, thereby leaving interstices in the material in the spaces previously occupied by the ice particles, and accordingly porous polysaccharide scaffolds are produced. Surprisingly, the cross-linking process occurs during the freeze-drying process.

The material density and pore size of the resultant scaffold may be therefore varied by controlling the rate of freeze-drying of the frozen aqueous solution. The essential parameter in a freeze-drying process is the vacuum rate.

For the purpose of the present invention, any type of polysaccharide can be used. Synthetic or natural polysaccharide may be alternatively used in the context of the invention. Non-limiting examples of suitable polysaccharide for implementing the present invention are dextran, agar, alginic acid, hyaluronic acid, inulin, pullulan, heparin, fucoidan, chitosan, scleroglucan, curdlan, starch, cellulose and mixtures thereof. Chemically modified polysaccharides bearing for instance acidic groups (carboxylate, sulphate, phosphate), amino groups (ethylene amine, diethylaminoethylamine, propylamine), hydrophobic groups (alkyl, benzyl) can be included. Saccharide structures and oligosaccharides that may be used to produce the desired materials include but are not limited to ribose, glucose, mannose, galactose, fructose, sorbose, sorbitol, mannitol, iditol, dulcitol and mixtures thereof. Many of these compounds are available commercially from companies such as Sigma-Aldrich (St. Louis, Mich., US).

Typically, the average molecular weight of the polysaccharides is from about 5,000 Daltons to about 2,000,000 Daltons, preferably from about 100,000 Daltons to about 500,000 Daltons. Typically, the polysaccharide used to prepare the scaffold of the invention is a neutral polysaccharide such as dextran, agar, pullulan, inulin, scleroglucan, curdlan, starch, cellulose and mixtures thereof. Alternatively, the polysaccharide used to prepare the scaffold of the invention is a positively charged polysaccharide such as chitosan, DEAE-dextran, DEAE-pullulan, EA-pullulan and mixtures thereof. Alternatively, the polysaccharide used to prepare the scaffold of the invention is a negatively charged polysaccharide such as alginic acid, hyaluronic acid, heparin, fucoidan and mixtures thereof. Alternatively, the polysaccharide used to prepare the scaffold of the invention is a mixture of neutral and negatively charged polysaccharides. Typically, the negatively charged polysaccharides represent 1 to 20%, preferably 5 to 10% of the mixture. Alternatively, the polysaccharide used to prepare the scaffold of the invention is a mixture of neutral and positively charged polysaccharides. Typically, the positively charged polysaccharides represent 1 to 20%, preferably 5 to 10% of the mixture.

Preferably, for the purpose of the invention, said polysaccharide is selected in the group consisting of dextran, pullulan, agar, alginic acid, starch, hyaluronic acid, inulin, heparin, fucoidan, chitosan and mixtures thereof. In one particular embodiment of the invention, said polysaccharide is a mixture of pullulan and dextran. Typically, the weight ratio of pullulan/dextran is in a range from 95:5 to 95:5 (w/w), preferably in a ration of 75:25 (w/w). In another embodiment of the invention, said polysaccharide is a mixture of pullulan, dextran and fucoidan. Typically, the weight ratio of pullulan/dextran/fucoidan is in a range from about 70:20:10 to about 50:20:30, preferably from about 70:20:10 to about 50:30:20, and most preferably in a ratio of about 73:22:5 (w/w). The presence of fucoidan in the porous polysaccharide scaffold of the invention is highly advantageous since fucoidan promotes vascularisation.

Typically, the covalent cross-linking agent is selected from the group consisting of trisodium trimetaphosphate (STMP), phosphorus oxychloride ($POCl_3$), epichlorohydrin, formaldehydes, carbodiimides, glutaraldehydes, any other compound that is suitable for crosslinking a polysaccharide and mixtures thereof. Many of these compounds are available commercially from companies such as Sigma-Aldrich (St. Louis, Mich., US). Preferably, for the purpose of the present invention, said cross-linking agent is STMP. Typically, the concentration of the covalent cross-linking agent in the aqueous solution (w/v) is from about 1% to about 6%, more preferably from about 2% to about 6%, most preferably from about 2% to about 3%. Typically, the weight ratio of the polysaccharide to the cross-linking agent is in a range from 20:1 to 1:1, preferably from 10:1 to 2:1.

In the context of the present invention, nano-hydroxyapatite may be a commercial nano-hydroxyapatite, such as those commercialised by Inframat Corporation or Fluidinova. Preferably, nanocristalline hydroxyapatite useful in the context of the present invention is obtained through chemical precipitation at room temperature of a solution of phosphoric acid, at a concentration comprised between 0.3 to 1M, preferably 0.6M, with a solution of calcium hydroxide, at a concentration comprised between 0.5 to 1.5M, preferably 1M. Typically, the concentration of hydroxyapatite in the alkaline solution of polysaccharide (w/v) is comprised between 0.01 and 10% (w/v), preferably between 0.1 and 0.5% (w/v), more preferably between 0.1 and 0.3% (w/v). Typically, the concentration of nano-hydroxyapatite in the alkaline solution of polysaccharide (w/v) is comprised between 0.01 and 10% (w/v), preferably between 0.1 and 0.5% (w/v), more preferably between 0.1 and 0.3% (w/v).

In one embodiment, the alkaline aqueous solution of step a) or step i) comprising hydroxyapatite, preferably nano-hydroxyapatite, may be poured in a mould before step b) or step ii), so that the porous polysaccharide scaffold obtained with the method of the invention can take a desired form. Any geometrical moulds may be used according to the invention. Different sizes may also be envisaged. The mould may be made of any material, but preferred material includes non sticky surfaces such as Teflon.

Alternatively, the scaffolds of the invention may be cut and shaped to take a desired size and form.

The methods of the invention can further include the step of sterilizing the scaffold using any suitable process. The scaffold can be sterilized at any suitable point, but preferably is sterilized before the scaffold is hydrated. A suitable irradiative sterilization technique is for example an irradiation with Cesium 137, 35 Gray for 10 minutes. Suitable non-irradiative sterilization techniques include, but are not limited to, UV-exposure, gas plasma or ethylene oxide methods known in the art. For example, the scaffold can be sterilized using a sterilisation system which is available from Abtox, Inc of Mundelein, Ill. under the trade mark PlazLyte, or in accordance with the gas plasma sterilization processes disclosed in U.S. Pat. No. 5,413,760 and U.S. Pat. No. 5,603,895.

The scaffold produced by the methods of the invention can be packaged in any suitable packaging material. Desirably, the packaging material maintains the sterility of the scaffold until the packaging material is breached.

In a further embodiment, the alkaline solution of step i) or a) further comprises a drug. The invention thus provides porous polysaccharide scaffold comprising a drug. Typically, said drug is a drug having an acknowledged therapeutic effect, such as hormones radioactive substance, fluorescent substance, chemotactic agent, antibiotic, steroidal or non-steroidal analgesic, immunosuppressant, or anti-cancer drug, drugs belonging to the pharmaceutical class of statins. Preferably, said drug belongs to the pharmaceutical class of statins. As used herein, "statins" refers to a pharmaceutical class of HMG-CoA reductase inhibitors. It has been recently shown that some of the drugs from this pharmaceutical class play a role in the process of bone formation. Preferably, said statins is selected from the group consisting of lovastatin, atorvastatin, mevastatin pitavastatin, rosuvastatin, pravastatin, fluvastatin and simvastatin. More preferably, said statins is selected from the group consisting of lovastatin, atorvastatin, mevastatin and simvastatin. Said statins are highly appropriate in the context of the present invention since they play a role in the bone formation.

In a further embodiment, the alkaline solution further comprises a bioactive substance. Typically, said bioactive substance is a substance known for playing an important role in various mechanisms such as modification of cellular pathways and modification of cellular or tissular responses. Said bioactive substance is chosen among growth factors, cytokines (lymphokines, interleukins, and chemokines), antioxidant molecules, angiogenic molecule, anti-angiogenic agents, immunomodulating agents, proinflammatory cytokines, anti inflammatory cytokines, plasma-derived bioactive substances, PRP (platelet rich plasma)-derived substances, soluble adhesion molecules.

In a third aspect, the invention relates to porous polysaccharide scaffolds obtainable by the methods of the invention. These porous polysaccharide scaffolds are indeed the only ones which have the remarkable properties provided by the invention. When the method of preparing the porous polysaccharide scaffold according to the invention involves the use of a porogen agent, the concentration of the porogen agent affects the size of the pores formed in the scaffolds. Therefore, in this particular embodiment, the size of the pores can be under the control of the concentration of said porogen agent. Typically, the average pore size of the scaffold is from about 1 µm to about 500 µm, preferably from about 10 µm to about 200 µm. Typically, the density of the pores (or porosity) is from about 4% to about 75%, preferably from about 4% to about 50%. The person skilled in the art may provide desired properties to the porous polysaccharide scaffold according to the invention. Typically, the person skilled in the art may add one or more compounds chosen in the group consisting of a biomolecule, a bioactive agent, a drug, an anti-inflammatory agent, an additive, an antimicrobial agent, a colorant, a surfactant and a differentiation agent. The techniques for incorporating said compounds in the porous polysaccharide scaffold of the invention completely falls within the ability of the person skilled in the art. Typically, said compounds may be added directly the alkaline solution of step i) or a) of the method of the invention. In this particular embodiment, the compound would be within the structure of the porous polysaccharide scaffold of the invention. Alternatively, said compounds can be incorporated into the porous polysaccharide scaffold during a step consisting of hydrating said scaffold with a solution of the compound.

In one embodiment, the porous polysaccharide scaffold of the invention further comprises one or more biomolecules. Non-limiting examples of biomolecules are drugs, hormones, radioactive substances, fluorescent substances, chemicals or agents, chemotactic agents, antibiotics, steroidal or non-steroidal analgesics, immunosuppressants, anti-cancer drugs, short chain peptides, glycoprotein, lipoprotein, cell attachment mediators, biologically active ligands, integrin binding sequence, ligands, small molecules that affect the up-regulation of specific growth factors, tenascin-C, hyaluronic acid, chondroitin sulphate, fibronectin, decorin, thromboelastin, thrombin-derived peptides, and mixtures thereof. The presence of said biomolecules in the porous polysaccharide scaffold of the invention may enhance treatment effects, enhance visualization, indicate proper orientation, resist infection, promote healing, may increase softness or any other desirable effects. In another embodiment, the porous polysaccharide scaffold of the invention further comprises a bioactive substance. Typically, said bioactive substance is a substance known for playing an important role in various mechanisms such as modification of cellular pathways and modification of cellular or tissular responses. Said bioactive substance is chosen among growth factors, cytokines (lymphokines, interleukins, and chemokines), antioxidant molecules, angiogenic molecule, anti-angiogenic agents, immunomodulating agents, proinflammatory cytokines, antiinflammatory cytokines, plasma-derived bioactive substances, PRP (platelet rich plasma)-derived substances, and soluble adhesion molecules.

In a further embodiment, the porous polysaccharide scaffold of the invention further comprises one or more drug. Typically, said drug is a drug having an acknowledged therapeutic effect, such as hormones radioactive substance, fluorescent substance, chemotactic agent, antibiotic, steroidal or non-steroidal analgesic, immunosuppressant, or anti-cancer drug, drugs belonging to the pharmaceutical class of statins. Preferably, said drug belongs to the pharmaceutical class of statins. Preferably, said statins is selected from the group consisting of lovastatin, atorvastatin, mevastatin pitavastatin, rosuvastatin, pravastatin, fluvastatin and simvastatin. More preferably, said statins is selected from the group consisting of lovastatin, atorvastatin, mevastatin and simvastatin. Said statins are highly appropriate in the context of the present invention since they play a role in the bone formation In another embodiment, the porous polysaccharide scaffold of the invention further comprises anti-inflammatory agents. Non-limiting examples of anti-inflammatory agents are indomethacin, salicylic acid acetate, ibuprofen, sulindac, piroxicam, and naproxen; thrombogenic agents, such as thrombin, fibrinogen, homocysteine, and estramustine; and radio-opaque compounds, such as barium sulfate, gold particles and iron oxide nanoparticles (USPIOs) and mixtures thereof.

In still another embodiment, the porous polysaccharide scaffold of the invention further comprises additives. The amount of the additive used depends on the particular application of the porous polysaccharide scaffold of the invention and may be readily determined by the person skilled in the art using routine experimentation.

In still another embodiment, the porous polysaccharide scaffold of the invention further comprises an antimicrobial agent. Suitable antimicrobial agents are well known in the art. Non-limiting examples of suitable antimicrobial agents are alkyl parabens, such as methylparaben, ethylparaben, propylparaben, and butylparaben; cresol; chlorocresol; hydroquinone; sodium benzoate; potassium benzoate; triclosan and chlorhexidine and mixture thereof. Other examples of antibacterial agents and of anti-infectious agents that may be used are, in a non-limiting manner, rifampicin, minocycline, chlorhexidine, silver ion agents and silver-based compositions and mixtures thereof.

In a further embodiment, the porous polysaccharide scaffold of the invention further comprises at least one colorant to enhance the visibility of the scaffold. Suitable colorants include dyes, pigments, and natural coloring agents. Non-limiting examples of suitable colorants are alcian blue, fluorescein isothiocyanate (FITC) and FITC dextran and mixtures thereof.

In still another embodiment, the porous polysaccharide scaffold of the invention further comprises at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan and mixtures thereof.

In one embodiment, the porous polysaccharide scaffold of the invention further comprises a differentiation agent. Preferably, such a differentiation agent is an agent involved in bone formation. Alternatively, such a differentiation agent is an agent involved in osteogenesis, angiogenesis or wound healing. Preferably, such a differentiation agent is a growth factor. Non-limiting examples of growth factor suitable for the purpose of the present invention are epidermal growth factor (EGF), insulin-like growth factor (IGF-I, IGF-II), transforming growth factor beta (TGFβ), heparin binding growth factor (HBGF), stromal derived factor (SDF-1), vascular endothelial growth factors (VEGF), fibroblast growth factors (FGFs), platelet derived growth factors (PDGF), parathyroid hormone (PTH), parathyroid hormone related peptide (PTHrP), basic fibroblast growth factor (bFGF); TGFβ superfamily factors; bone morphogenetic proteins (BMPs) preferably BMP2, BMP3, BMP4, BMP5, BMP7, somatropin, growth differentiation factor (GDF) and mixtures thereof.

Typically, the growth factor is present at a concentration comprised from 1 ng to 100 µg per porous polysaccharide scaffold of the invention.

In another embodiment, the porous polysaccharide scaffold of the invention further comprises cells, such as yeast cells, mammalian cells, insect cells, and plant cells.

Preferably, said cell is a mammalian cell. Non-limiting examples of mammalian cells suitable for the purpose of the invention are differentiated cells such as chondrocytes, fibrochondrocytes, osteocytes, osteoblasts, osteoclasts, synoviocytes, epithelial cells and hepatocytes or stem cells, embryonic stem cells, induced progenitor stem cells (iPS), mesenchymal stem cells from different sources, bone marrow, adipose tissue, peripheral blood progenitor cells, cord blood progenitor cells, genetically transformed cells and mixtures thereof. Most preferably, the mammalian cells comprised in the porous polysaccharide scaffold according to the invention are adipose derived stroma cells. Typically, the mammalian cells comprised in the porous polysaccharide scaffold are present at a cell density comprised between 200 cells/mm$^3$ to 35 000 cells/mm$^3$.

In a fourth aspect, the invention relates to a porous polysaccharide scaffold obtainable according to the method of the invention for use for bone generation.

As used herein, the expression "bone generation" encompasses "bone repair" and "bone development".

In a fifth aspect, the invention relates to a porous polysaccharide scaffold obtainable according to the method of the invention for use for stimulating ectopic mineralized tissue formation. In the context of the present invention, the expression "ectopic" refers to a non osseous tissue. Therefore, the invention also relates to a porous polysaccharide scaffold obtainable according to the method of the invention for use for inducing mineralized tissue in a non-osseous site.

Preferably, said stimulation of ectopic mineralization occurs in absence of stem cells and/or growth factors. Indeed, the inventors have shown that the porous polysaccharide scaffold according to the invention has the ability to induce mineralized tissue in a non-osseous site and in an osseous site (calvaria site or femoral condyle), even in the absence of stem cells and/or growth factors. Therefore, the invention provides a porous polysaccharide scaffold useful for stimulating mineralized tissue formation in osseous site, as well as in non-osseous site, in the presence as well as in the absence of stem cells and/or growth factors.

Use of the Porous Polysaccharide Scaffold According to the Invention

The inventors have shown that implanting porous polysaccharide scaffold according to the invention lead to the stimulation of a dense collagen network and blood vessel formation as well as the recruitment of osteoblast-like cells. Said implantation of scaffolds according to the invention in subcutaneous site leads to the formation of a dense mineralized tissue, and thus to bone formation.

The inventors have shown that the scaffold of the invention, when implanted, retains growth factor such as VEGF and BMP. The inventors also evidenced that the ability of retaining said growth factor was higher for the scaffold comprising n-HA, compared to a scaffold not comprising n-HA.

In a sixth aspect, the invention relates to a porous polysaccharide scaffold obtainable according to the method of the invention for use in the treatment of bone related disorders. The inventors have indeed shown the ability of the porous polysaccharide scaffold according to the invention to stimulate the production of an extracellular mineralized matrix, probably through differentiation of cells into bone cells. Thus, the inventors evidenced that the scaffold of the invention is useful for the treatment of bone related disorders.

In a seventh aspect, the invention relates to a porous polysaccharide scaffold obtainable according to the method of the invention for use as a polysaccharide scaffold.

Typically, the size and the shape of the porous polysaccharide scaffold can be adapted to the type and size of the bone to replace, and to the localization of said bone. Preferably, the shape of the scaffold is a sphere, a cylinder, a cube or a rectangular cuboid. Preferably, the size of said scaffold is comprised between 0.5 mm and 30 cm. Typically, the polysaccharide scaffold of the invention may be is implanted as follows: the lyophilized scaffold is placed within the defect and its size is adapted to the size of defect. For example, for the implantation in calvaria site in mouse, defects of 4 mm of diameter and 500 vim of depth were performed and the matrices were apposed onto the host tissue. In mice, bone defect performed in the femoral condyle is around 1 mm$^3$. In rat, the critical size defect performed in the femoral condyle is 5 mm of diameter and 3 mm of depth. These bone defects are filled with the matrices. For segmental bone defect in large animal (sheep or goat), a resection of 2.5 cm is performed at metatarsus and cylinder of polysaccharide scaffold is placed within the defect. Analysis of the newly formed tissue within the defect is performed between 15 days to 12 months. The person skilled in the art is award of the routine suitable techniques for analyzing said newly formed tissue. Typically, said analysis may be performed using several invasive methods such as histomorphometry as gold standard technique. Alternatively, said analysis may be performed using non invasive imaging approaches such as Magnetic Resonance Imaging (MRI), X Ray micro Computed Tomography (micro-CT), Single Photon Emission Computarized Tomography (SPECT) or radiological analysis. The choice of the suitable technique is dependent on the type of bone in small and large animals, or humans.

FIGURES LEGENDS

FIG. 1: Porous polysaccharide scaffold.

Macroscopic view of hybrid porous discs with n-HA before (FIG. 1A) and after (FIG. 1B) rehydration with phosphate buffer saline (PBS). The scale bar corresponds to 1 mm.

Figure 2:
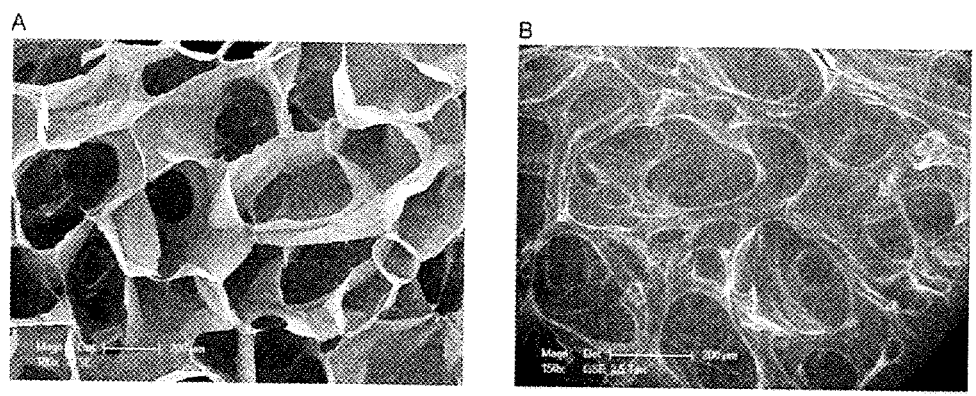

FIG. 2: Electron Microscopy of a freeze-dried polysaccharide scaffold.

The morphology of freeze-dried scaffolds was analyzed by scanning electron microscopy (FIG. 2A). After rehydration in PBS, porosity of hydrated scaffolds was observed with Environmental Scanning Electron Microscopy (ESEM Philips XL 30) (FIG. 2B).

Figure 3:
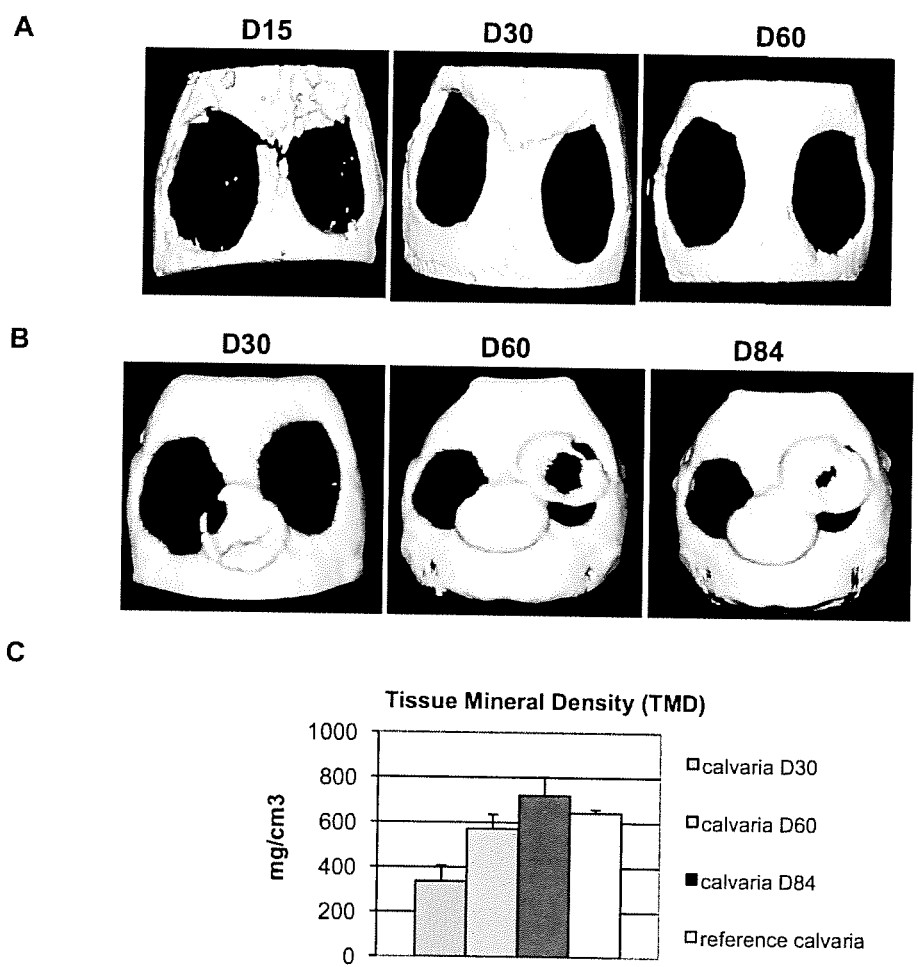

FIG. 3: Healing of critical size defects in nude mice by the polysaccharide-based matrices.

Micro-CT images of calvaria defects filled with polysaccharide matrices without n-HA (FIG. 3A), or with the polysaccharide scaffold (FIG. 3B), loaded (on left side) or not (on right side) with 5×10$^5$ differentiated adipose derived stromal cells (ADSCs). Imaging on the same animal for each type of scaffold was performed after 15, 30, 60 and 84 days of implantation, and resulting images are respectively referred to as D15, D30, D60, D84. Quantitative analysis of the Tissue Mineral Density (TMD) of implanted polysaccharide scaffold. Calvaria bone was used as a control (FIG. 3C).

Figure 4:
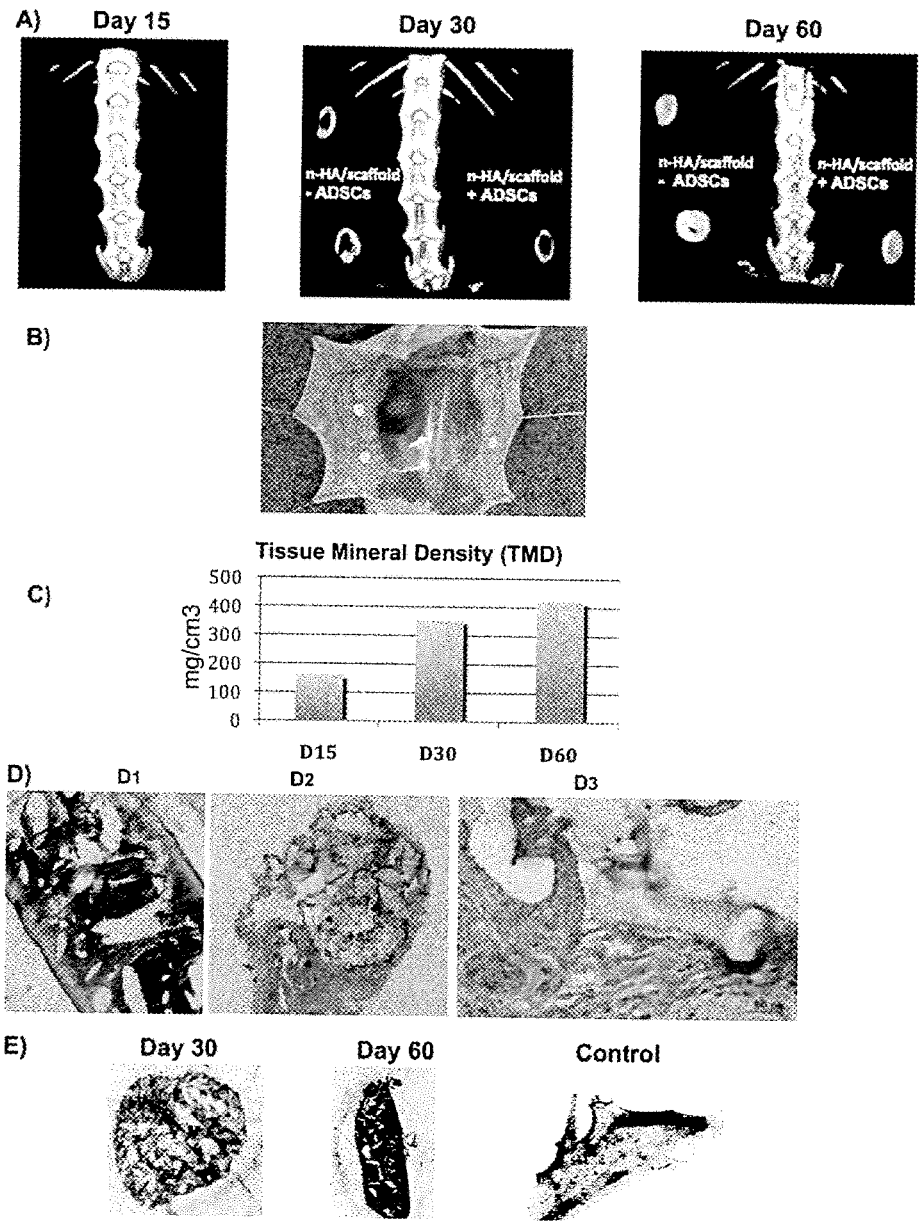

FIG. 4: Ectopic mineralized tissue formation in subcutaneous site induced by the polysaccharide scaffold.

(A) Micro-CT images at Days 15, 30 and 60 of a mouse implanted with two discs of the polysaccharide scaffold (n-HA/scaffold) (left site) and one disc previously seeded with 5×10$^5$ differentiated ADSCs (right site).

(B) Macroscopic view at D60.

(C) Quantitative analysis of the tissue mineral density (TMD).

(D) Histological examination of undecalcified (D1; magnification ×10) (stained by Goldner's trichrome) and decalcified (D2; magnification ×2) (D3; magnification ×20) sections (Masson's staining) obtained at Day 60.

(E) Von Kossa staining performed on explanted materials at Day 30 and Day 60. Control was performed using the paraffin-embedded composite matrix before implantation (magnification ×2).

Figure 5:
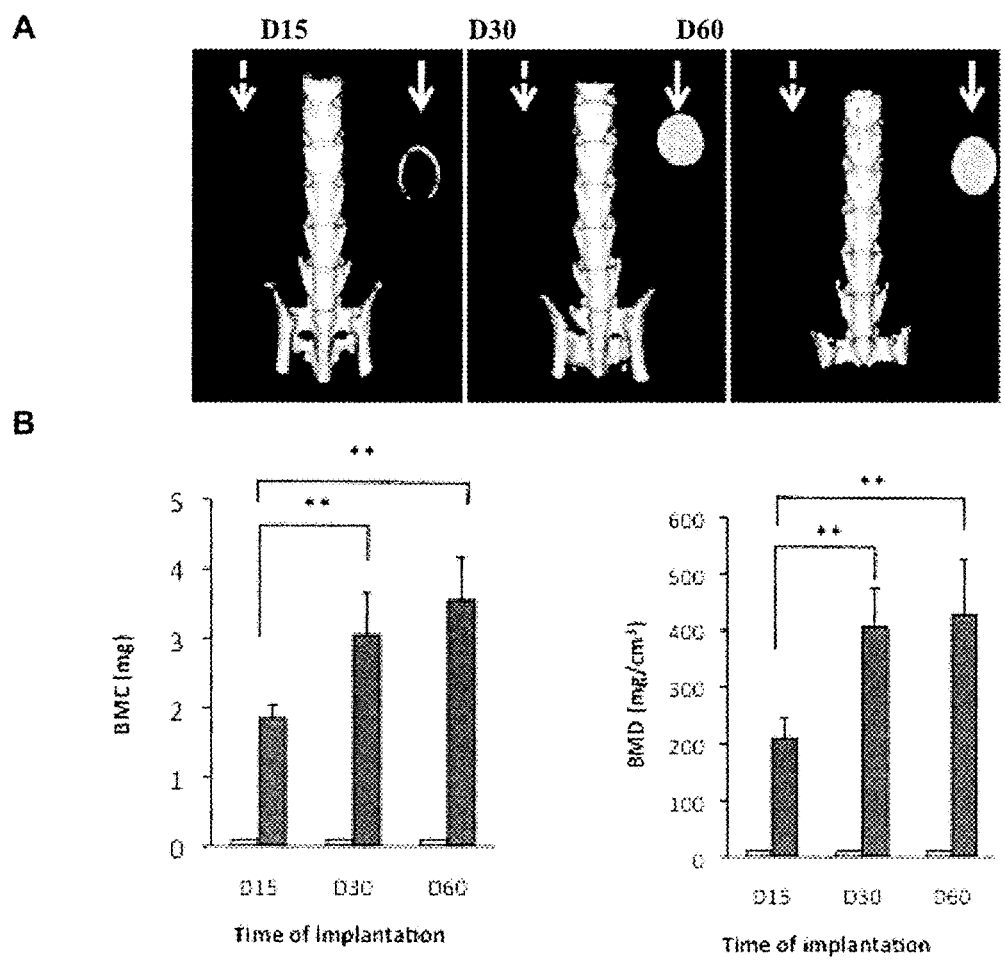

FIG. 5: Matrix+n-HA (MATRI+) induces mineralization in ectopic site of mice.

(A) Representative micro-CT images of the subcutaneous implantation of the Matrix alone on the left side (indicated by an arrowed doted line) and Matrix+n-HA (MATRI+) on right side (indicated by an arrowed plain line), after 15 (D15), 30 (D30) and 60 days (D60) of implantation in Balb/c mice.

(B) Bone Mineral Content (BMC) and Bone Mineral Density (BMD) were measured from reconstructed three-dimensional micro-CT images with Microview Image analyser of the Matrix (white rectangle) and Matrix+n-HA (MATRI+) (black rectangle). Data are presented as means±standard deviation for n=8. The symbol ** indicates a statistically significant difference compared to the other groups <0.01.

Figure 6:
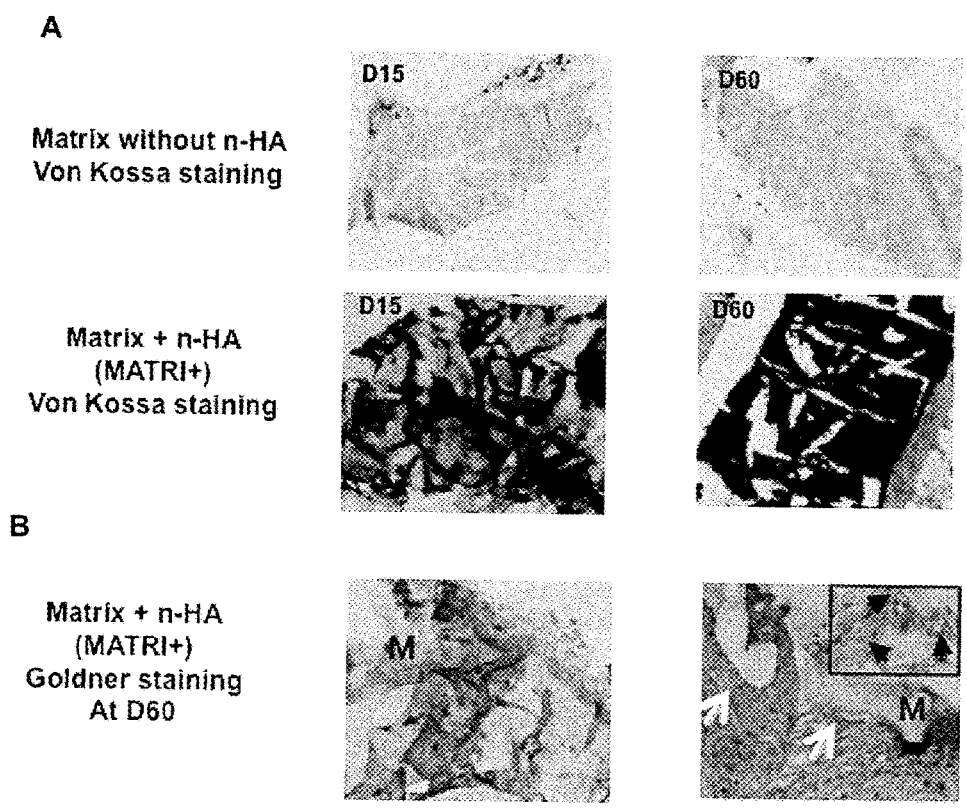

FIG. 6: Matrix+n-HA induces formation of a collagen-based mineralized tissue: histological analysis of the newly formed tissue.

(A) Representative histological undecalcified sections of the Matrix and Matrix+n-HA (MATRI+) samples implanted subcutaneously in mice, after 15 days (D15) and 60 days (D60): Von Kossa staining.

(B) Representative histological decalcified sections of Matrix+n-HA (MATRI+) 60 days after implantation:Goldner staining, The images showed a high dense collagen tissue around the implant that colonizes the scaffold, with osteoblast-like cells as indicated by the white arrows, and numerous vessels inside the collagen tissue indicated by the black arrows.

Figure 7:
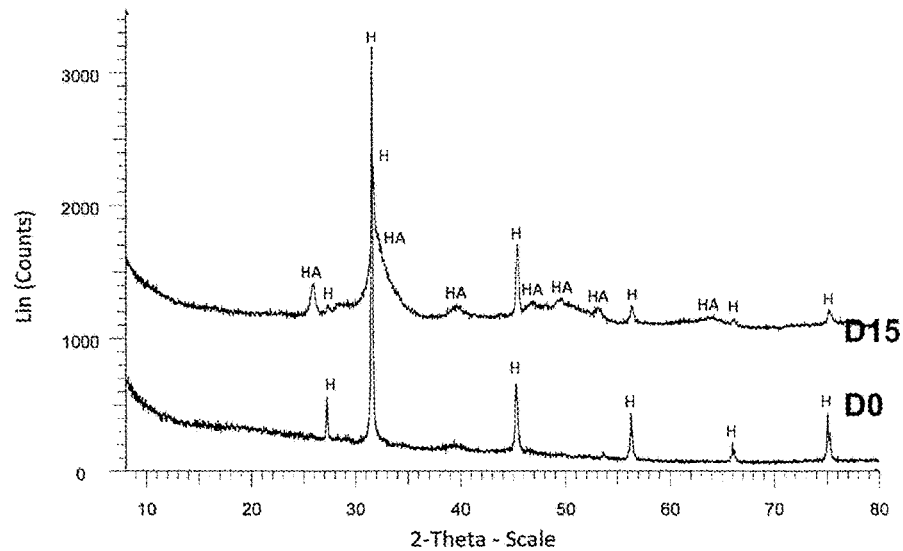
Figure 7:
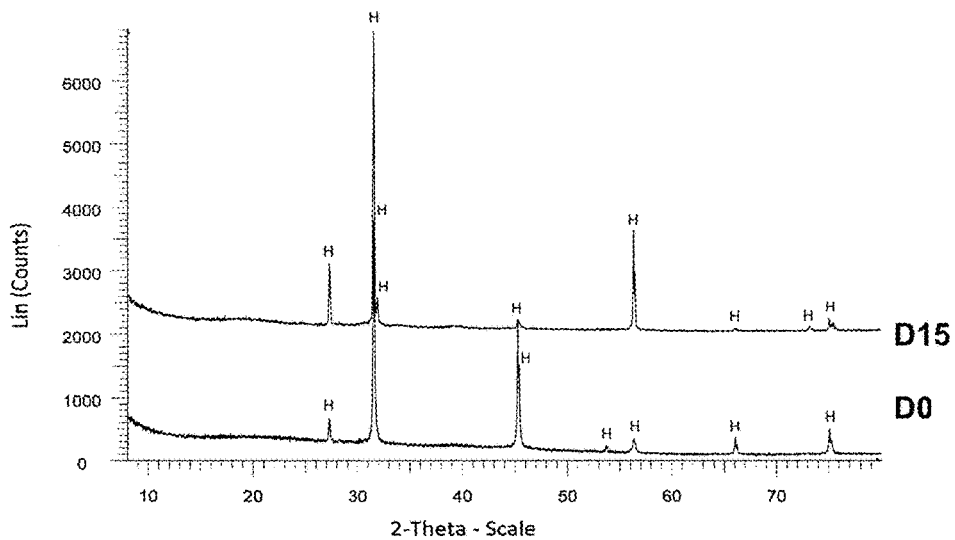

FIG. 7: XRD patterns of matrices before surgery (D0) and 15 days (D15) after subcutaneously implantation in mice.

(A) Matrix+n-HA (MATRI+); (B) Matrix without n-HA

Specific peaks of hydroxyapatite (HA) are only observed in the XRD patterns after 15 days of implantation of MATRI+. Peaks of Halite (H) due to sample processing, are observed in all spectra. The XRD patterns obtained at day 30 and day 60 are similar than those observed at D15 for both groups (data not shown).

Figure 8:
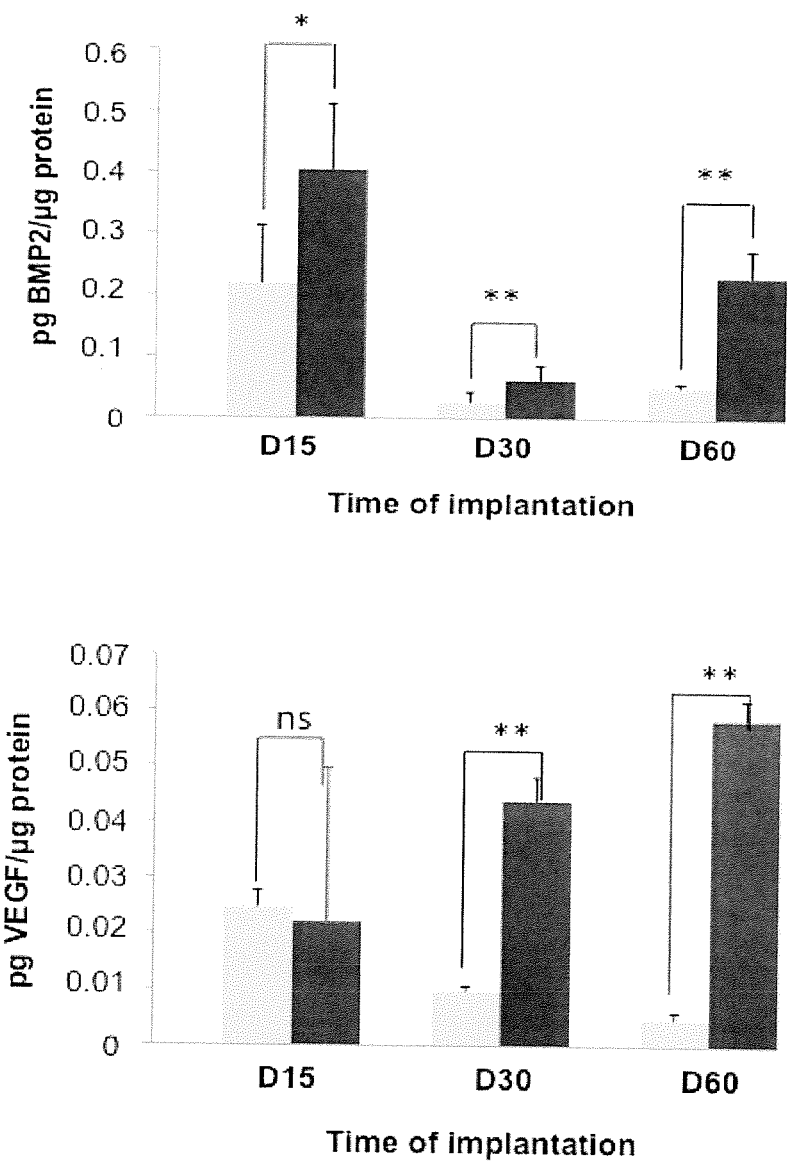

FIG. 8: Matrix+n-HA (MATRI+) retained endogeneous osteoinductive and angiogenic factors.

Measurement by ELISA of BMP2 (A) and VEGF$_{165}$ (B), retained in the tissue formed within the Matrix (white rectangle) and Matrix+n-HA (MATRI+) (black rectangle) when implanted subcutaneously at D15, D30 and D60. Results are expressed in pg of growth factors retained per µg of proteins quantified by BCA. Data are presented as means±standard deviation for n=6 samples. The symbols * and ** indicate a statistically significant difference compared to the other groups with p<0.05 and <0.01, respectively.

Figure 9:
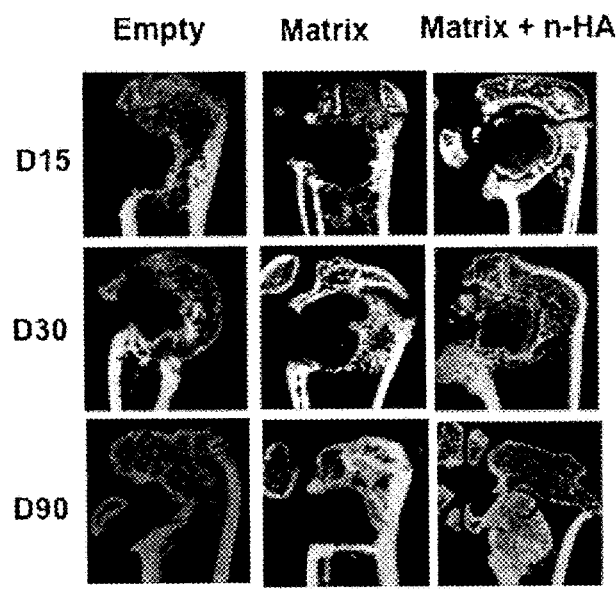
Figure 9:
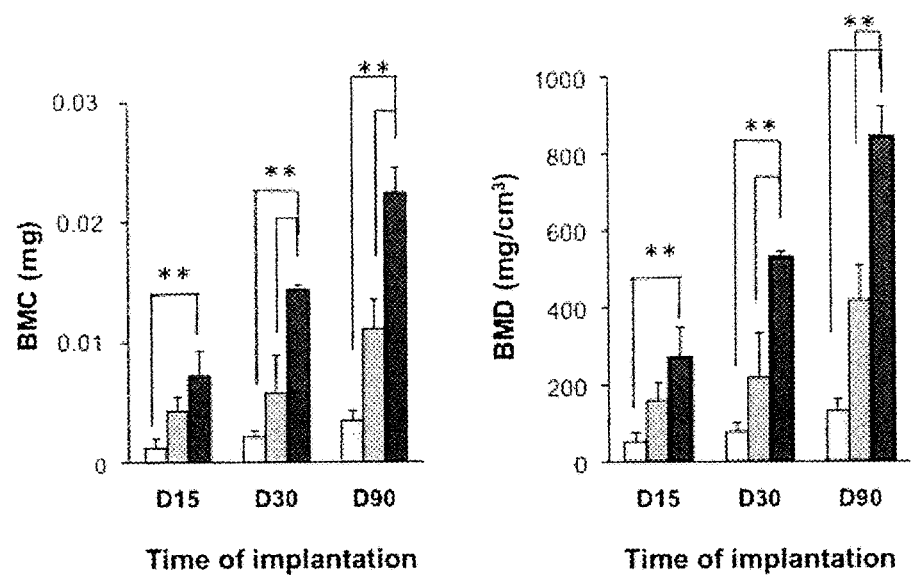

FIG. 9: Matrix+n-HA (MATRI+) induces a high mineralization of tissue in a critical size bone defect performed in the femoral condyle of rats.

(A) Representative micro-CT images of the femoral condyle of rats, 15 days (D15), 30 days (D30) and 90 days (D90) after implantation without scaffold (empty), with Matrix or Matrix+n-HA (MATRI+).

(B) Bone Mineral Content (BMC) and Bone Mineral Density (BMD) were measured from reconstructed three-dimensional micro-CT images of the empty group (white rectangle), the Matrix group (grey rectangle) and Matrix+n-HA (MATRI+) (black rectangle). Data are presented as means±standard deviation for n=4. The symbol ** indicates a statistically significant difference compared to the other groups with p<0.01.

Figure 10:
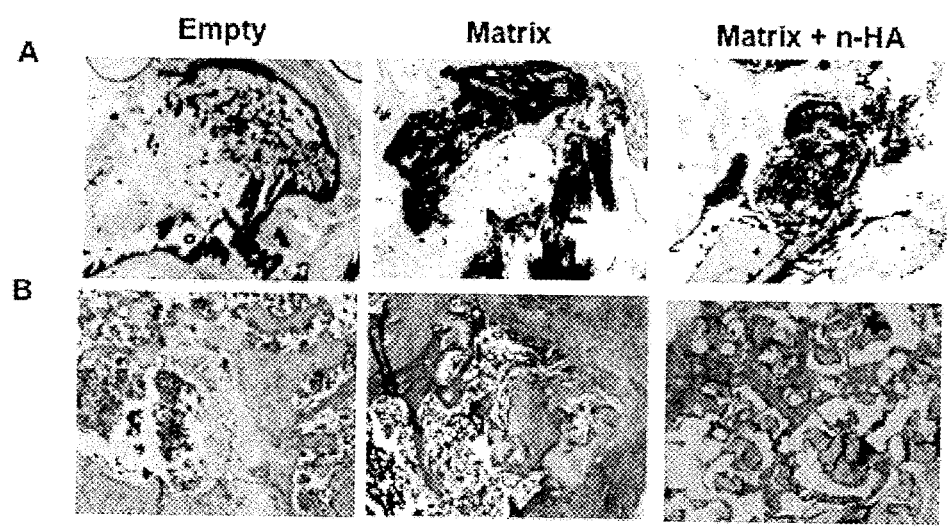

FIG. 10: Matrix+nHA (MATRI+) induces a high mineralized bone tissue in a critical size bone defect performed in the femoral condyle of rats after 90 days of implantation; histological analysis of the newly formed tissue.

(A) Representative histological undecalcified sections of Empty, Matrix and Matrix+n-HA (MATRI+) samples implanted in the femoral condyle of rats, after 90 days of implantation: Von Kossa staining. The arrows indicated the position of the bone defect.

(B) Representative histological decalcified sections of Empty, Matrix and Matrix+nHA samples 90 days after implantation:Goldner staining, A fibrous tissue was formed in the empty bone defect, while bone formation occurred in direct contact of the matrix and was enhanced within the MATRIX+ implant.

EXAMPLE

Example 1: Implantation of the Scaffold of the Invention in Calvaria Site of Athymic Mice Materials and Methods
Nano-Hydroxyapatite Preparation Nano-hydroxyapatite (n-HA) was prepared by wet chemical precipitation using a 0.6M solution of Phosphoric acid ($H_3PO_4$ Rectapur, Prolabo®, France) and a 1M solution of calcium hydroxide ($CaOH_2$ Alfa Aesar, Germany). 100 ml of $H_3PO_4$ solution were added dropwise in 100 ml of $CaOH_2$ solution during 30 minutes under vigorous stirring at room temperature. At the end of reaction, pH was adjusted to 9 using $0.4.10^{-3}$ mol of a 0.6 M sodium hydroxide solution, then stirring was continued during 12 hours.

Nano-hydroxyapatite (n-HA) has been characterized by transmission electron microscopy (TEM), scanning electron microscopy and by FTIR analysis. TEM revealed n-HA needle-shaped crystals of 50 nm long. FTIR analysis showed specific bands of phosphate ions of at 559 $cm^{-1}$, 601 $cm^{-1}$ and 1018 $cm^{-1}$ and a non-specific carbonate band 1415 $cm^{-1}$.

Preparation of Composite Polysaccharide Scaffolds (MATRI+)

Macroporous composite scaffolds (MATRI+) were prepared using a blend of pullulan/dextran 75:25 (pullulan, MW 200,000, Hayashibara Inc, Dextran MW 500,000, Pharmacia), prepared by dissolving 9 g of pullulan and 3 g of dextran into 27 mL of distilled water containing 14 g of NaCl and 13 mL of nano-hydroxyapatite suspension (n-HA, 6.36% w/v). Chemical cross-linking was carried out using trisodium trimetaphosphate STMP (Sigma) under alkaline condition. Briefly, 1 mL of 10M sodium hydroxide was added to 10 g of the polysaccharide blend, followed by the addition of 1 mL of water containing 300 mg of STMP. After incubation at 50° C. for 15 min, resulting scaffolds were cut into 6 mm diameter discs, neutralized in PBS 10× (pH 7.4) then washed extensively with a 0.025% NaCl solution. After a freeze-drying step, porous composite polysaccharide scaffolds were stored at room temperature until use. Fluorescent scaffolds were prepared by adding 1% of Fluorescein Iso-ThioCyanate (FITC) dextran (Sigma, St. Louis Mo., USA) to the mixture before cross-linking.

ADSC Cultures and Osteogenic Differentiation

Adipose Derived Stromal Cells (ADSCs) were isolated from human adipose tissue after a digestion with 0.1% (w/v) collagenase type I and cultured as previously described by Gimble et al, 2007. The remaining Stromal Vascular Fraction (SVF) was cultured in a basal medium (DMEM F12 medium (Invitrogen) supplemented with 10% (v/v) Foetal Bovine Serum (FBS) or in an osteogenic medium for inducing osteoblastic differentiation of ADSCs (IMDM medium (Invitrogen), supplemented with 10% (v/v) FBS (Lonza), $10^{-8}$ M dexamethasone (Sigma), 50 mg/ml ascorbic acid (Sigma) and 10 mM β-glycerophosphate (Sigma)).

Experimental Models in Nude Mice

Orthotopic new bone formation was assessed on calvaria site of athymic mice. Twelve weeks-old nude mice were anesthetized with an isoflurane/N2O mixture and were subjected to surgery to make a 4 mm diameter full thickness on the left and right parietal bone using a trephine dental burr. Disk-shaped matrices without n-HA (Group 1) and composite polysaccharide scaffold MATRI+ containing n-HA (Group 2) were implanted on top of the periosteum of the parietal bone. Group 3 corresponds to mice implanted with the composite polysaccharide scaffold associated with differentiated ADSCs one week before implantation.

To study ectopic bone formation, polysaccharide-based matrices (Group 1), composite polysaccharidescaffold without cells (Group 2), or matrices previously seeded with differentiated ADSCs (Group 3), were implanted into dorsal, subcutaneous spaces of athymic mice (female, 12 weeks old). Four scaffolds were implanted by mice. Bone formation was followed by a non invasive high resolution X-ray tomography (micro-CT) analysis performed 15, 30 and 60 days after implantation and by histological examination at the end of the experiment (D60).

High Resolution X-Ray Tomography (Micro-CT) Analysis

Mice were scanned in an in vivo Explore Locus SP X-Ray micro-computerized tomography (micro-CT) device (General Electric) at an isotropic resolution of 45 μm. Reconstruction of the parietal and subcutaneous region was performed following correction of rotation centre and calibration of mineral density. Bone analysis was performed using the "Advanced Bone Analysis"™ software (GE). Thresholding of grey values was performed using the histogram tool in order to separate mineralized elements from background. The density of mineralized tissue (TMD) was determined in the region of interest (ROI).

Histological Evaluation

At the end of the experimental periods, mice were euthanized and samples were dissected out and fixed in 3.7% (v/v) paraformaldehyde in PBS 0.1M pH 7.4. One part of the samples were decalcified and embedded in paraffin. Permanent sections of 7 micron were stained with hematoxylin and eosin and Masson trichrome dye. The other part of the samples were embedded in methylmethacrylate as described by Schenk et al, 1984. Longitudinal sections (15 μm thick) were prepared using a Leica microtome and tungsten carbide blades. Sections were stained with Goldner's trichrome, Von Kossa, and observed using a Nikon Eclipse 80i microscope. Pictures were generated using a DXM 1200 C (Nikon) CCD camera.

Results 3D porous matrices (FIG. 1) were obtained according to the methods disclosed in the PCT patent applications WO2009/047346 and WO2009/047347, with n-HA included in the starting formulation. n-HA in suspension (6.36% (w/v)) allowed an homogeneous dispersion of the HA nanoparticles in the resulting 3D matrices. The n-HA matrices contained in the dry state, 2.8+/−0.1% (w/w) of HA. The use of n-HA in the dry form instead of a n-HA suspension, induced large aggregates inside the matrices. The 3D matrices in the presence of n-HA are porous (FIG. 2) with pore sizes controlled by the patented process.

Discs of 4 mm in diameter of 3D porous matrices with or without n-HA (composite scaffold) and previously seeded or not with human adipose derived mesenchymal stem cells (ADSCs) were then evaluated in two mice models.

Orthotopic new bone formation on calvariae site of athymic mice revealed that only the polysaccharide-based matrices associated with n-HA (composite scaffold) induced formation of a mineralized tissue in nude mice. The porous matrices without n-HA do not induce any mineralization within 60 days. The orthotopic new bone formation was observed with composite matrices in absence of human mesenchymal stem cells, and even if the scaffold moved out of the bone defect (FIG. 3B). The mineralization occurred four weeks after implantation and increased with time (FIG.

3C). Histological examination (Goldner's trichrome staining) revealed a fibrous tissue formed when polysaccharide-based matrices without n-HA were implanted, whereas the composite polysaccharide scaffold provides an efficient scaffold for local production of collagen network within the matrices.

Since the n-HA matrix (composite scaffold) was found to induce mineralization outside the bone defect, the inventors next examined its potency to stimulate ectopic bone formation. They observed that implantation of matrices without n-HA did not form any mineralized tissue at day 60. In contrast, implantation of n-HA matrices (composite polysaccharide scaffold of the invention) in subcutaneous site lead to the formation of a dense mineralized tissue (FIGS. 4A and 4B) four weeks after implantation and without ADSCs seeding. The mineralization increased with time. Quantification indicated that the TMD of the calcified tissue was about 420 mg/cm$^3$ and close to the density of the implanted composite matrix in orthotopic site (FIG. 4C) 60 days after implantation. Histological analysis on undecalcified (FIG. 4D$_1$) and decalcified (FIG. 4D$_2$) sections of the ectopically induced mineralized tissue revealed that n-HA matrices (composite polysaccharide scaffold MATRI+) stimulated a dense collagen network and blood vessel formation as well as the recruitment of osteoblast-like cells (FIG. 4D$_3$). To visualize the level of calcification in the newly formed tissue, sections of n-HA/scaffold were stained according to Von Kossa technique at day 30 and day 60 (FIG. 4E). Controls were performed on the paraffin-embedded composite polysaccharide. This staining showed a well-calcified tissue of n-HA/scaffold that increases with time of implantation. To the knowledge of the inventors, no material so far in the absence of stem cells or growth factors, was able to give this effect.

The inventors further investigated for comparison the role of n-HA alone on non-osseous site. For this purpose, they proceed to the implantation of n-HA alone in subcutaneous site. After 15 days and 30 days, they only observed a classical reaction to a foreign body. Indeed, the histological examination of undecalcified section (Cyanine Solochrome staining) of non-osseous site implanted with n-HA alone did not show the presence of any mineralized tissue. Implantation of n-HA alone hence did not lead to the formation of a mineralized tissue.

The inventors have thus shown that the porous composite polysaccharide scaffold of the invention provides unexpected results by stimulating mineralized tissue formation in osseous site, as well as in non-osseous site, in the absence of stem cells or growth factors.

Example 2: Implantation of the Scaffold According to the Invention in a Non Osseous Site in Mice and Osseous Site in Rat Materials and Methods Nanohydroxyapatite and scaffold according to the invention were prepare as described in Example 1. The inventors assessed the implantation of said scaffold in animal. Both the procedure and the animal treatment complied with the Principles of Laboratory Animal Care formulated by the National Society for Medical Research. The studies were carried out in accredited animal facilities at the University of Bordeaux Segalen, under authorization (No.: 3300048 of the Ministere de l'Agriculture, France) and were approved by the Animal Research Committee of Bordeaux University.
Non-Osseous Implantation in Mice: Ectopic Bone Formation Analysis The two different formulations of scaffolds: disk-shaped matrices without n-HA (Group 1) and the composite scaffold containing n-HA (MATRI+) (Group2) (cylinders of 4 mm diameter and 6 mm depth) were inserted into subcutaneous pockets created in the dorsum of the 12-week-old Balb/c mice weighing 25-30 g (Charles River Laboratories, France). Samples were retrieved after 15, 30 and 60 days of implantation and treated for micro-CT and histological analysis. Eight samples were used for histological observation and micro-CT in each group.

Osseous Implantation in Rats: Orthotopic New Bone Formation Analysis

Medial holes, 5 mm diameter and 6 mm depth were created in both left and right femoral condyles of Wistar rats weighing 150-200 g (Charles River Laboratories, France) using trephine dental burr. Bone pieces were removed from the bone defect, the hole was rinsed with physiological solution (NaCl 0.9% (w/v) before introducing the scaffold within the defect. The two different scaffold formulations (matrices without n-HA and composite scaffold containing n-HA) were implanted into each bone defect. A control experiment without scaffold was also conducted. Implants were retrieved 15, 30, 60 and 90 days after surgery and treated for micro-CT and histological analysis. Six samples were used for micro-CT and histological observation in each group.

Histological Procedure

At the end of each implantation period, animals were euthanized by injecting an overdose of pentobarbital sodium (Nembutal®). Immediately afterwards, the implants and surrounding tissue were retrieved, fixed with 4% (w/v) paraformaldehyde in a 0.1 M phosphate buffer and scanned with micro-CT before histology. The samples were then prepared for histological analysis. One part was decalcified, dehydrated and embedded in paraffin. Thin sections (7 µm in thickness) were prepared and stained with hematoxylin and eosin and with Goldner's Trichrome for osteoid staining. The other part were dehydrated in a graded series of ethanol, and then embedded with methylmethacrylate, which was subsequently polymerized. Ten to 15 µm transverse sections were made using a modified diamond blade microtome (Leica Microsystems SP1600, Rijswijk, The Netherlands), with four sections obtained from each implant. Sections were stained with Goldner's trichrome, Von Kossa, and observed using a Nikon Eclipse 80i microscope. Pictures were generated using a DXM 1200 C (Nikon) CCD camera.

Micro-Computed Tomography (Micro-CT)

Micro-CT was used to develop three-dimensional images of the implants and surrounding tissue; these models were used to quantify the bone formation at each implant site. An ex vivo General Electric (GE) micro-CT (Explore LP Locus, General Electric), with a source voltage of 80 kV, a current of 60 µA, and 15 µm resolution, was used to acquire X-ray radiographs. In vivo micro-CT (General Electric) was performed with a source voltage of 150 mV, a current of 450 µA, and 45 µm resolution. After scanning, cross-sectional slices were reconstructed and 3D analyses were performed using Microview software. Each scan result was reconstructed using the same threshold values to distinguish bone and air. Bone Mineral Content (BMC) and Bone Mineral density (BMD) volume were measured for each group and statistically analyzed using the Student's t-test.

Protein Extraction from Subcutaneous Implants and ELISA Analysis of Osteogenic and Angiogenic Growth Factors Retained within the Implants Subcutaneous implants retrieved after 2, 15, 30 and 60 days of implantation were crushed on ice with an electric crusher in PBS containing a cocktail of protease inhibitors (10 µg/ml Aprotinine (Sigma), 10 µg/ml Leupeptin (Sigma) and 1 mM (4-(2-Aminoethyl)benzenesulfonyl fluoride hydrochloride (AEBSF) (Fluka). The lysates were then centrifuged at 16 000 rpm and 4° C. for 20 min. The supernatant was collected and then frozen at −80° C. for ELISA analysis. Quantification of the protein was performed using bicinchoninic acid (BCA) protein assay kit (Thermoscientific) described by Smith P K et al. (1985). Absorbance was read at 550 nm. There were eight matrices without n-HA (Group 1) and composite scaffold MATRI+ containing n-HA samples (Group 2), respectively for each time of implantation. The amounts of $VEGF_{165}$ and BMP2 retained within the two different formulations of implants were quantified with the mouse VEGF immunoassay kit (MMV00, Quantikine®, R&D systems), and BMP-2 immunoassay kit (DBP200, Quantikine CD, R&D systems), respectively.

X-Ray Diffraction Analysis

Subcutaneous implants of matrices without n-HA and composite scaffold MATRI+ containing n-HA were retrieved after 15, 30 and 60 days of implantation. In order to obtain a fine powder without any organic tissues, they were treated with bleach for 2 hours at room temperature and then centrifuged to keep only the pellet. Structural properties were explored by X-ray diffraction (XRD) using PANalytical X'pert MPD diffractometer (Bragg Brentano t-t geometry) equipped with a secondary monochromator and uses a copper radiation (mean $\lambda=1,5418$ A°), the working tension and intensity were 40 kV and 40 mA, respectively.

Samples were placed on a single-crystalline wafer sample holder made of silicium. Diffractograms were all measured with the same parameters: angular range from 8 to 80° (2t), step: 0.02°, measure time: one hour; Following X-ray diffraction (XRD) analysis of the material, phase identification through JCPDS-ICDD data (Diffract-Plus Eva Software, Bruker©) was compatible with a carbonated hydroxyapatite $[Ca10(PO4)3(CO3)0.01(OH)1.3]$, displaying hexagonal lattice parameters (a=9.3892 A°; c=6.9019 A°; $\alpha=\beta=90°$ and g=120°; space group:P63/m(176)).

Statistical Analysis

All data were expressed as means±standard deviation (SD) and were analyzed using standard analysis of Student's t-test. Differences were considered significant when $p\leq0.05$ (a) or $p\leq0.01$ (b).

Results

Two different scaffolds, matrices without n-HA (Group 1) and the composite scaffold MATRI+ containing n-HA (Group 2), were implanted in Balb/c mice for 15, 30 and 60 days. Micro-CT, quantification of mineralization (BMC and BMD analysis) and histological studies were performed for both groups. Implantation of matrices without n-HA did not form any mineralized tissue from day 15 to day 60, as showed by micro-CT (FIG. 5A) and BMC and BMD quantification (FIG. 5B). In contrast, implantation in subcutaneous site of matrices containing n-HA (without any cells and growth factors) lead to the formation of a dense mineralized tissue (FIG. 5A) as quantified by BMC (Bone Mineral Content) and BMD (Bone Mineral Density) measured at each time (FIG. 1B). The mineralization process starts at day 15 from the periphery of the scaffold (FIG. 1A) and lead to a high and dense mineralized tissue after 60 days of implantation.

From histological data, the porous n-HA matrices exhibited favorable mineralized tissue responses at D15 and D60, as demonstrated by von Kossa staining of undecalcified sections of MATRI+ (FIG. 6A), compared to matrix without n-HA. Von kossa staining is high after 60 days of implantation of MATRI+, compared to the same scaffold at day 15. The n-HA matrices before implantation stained with von kossa revealed a slight staining, due to the presence of the nanohydroxyapatite within the scaffold (not shown). However, the staining is much lower than that observed after 30 and 60 days of implantation.

Moreover, Goldner staining performed 60 days after implantation on decalcified sections of MATRI+ (FIG. 6B), revealed, a dense fibrous collagen tissue, mainly around the implant. Some collagen tissue penetrate within the scaffold, exhibiting some lining osteoblast-like cells indicated by white arrows, in contact with the scaffold and numerous vessels marked by black arrows on the histological picture. No inflammatory event was detectable with both scaffolds, whatever the time of implantation.

The XRD patterns of powder of n-HA matrices before implantation (D0) or retrieved at day 15 (D15) revealed specific peaks of hydroxyapatite at D15 on the spectrum (FIG. 7A). Peaks of Halite (H), probably due to the treatment of the samples with bleach, were observed in all spectra. The XRD patterns obtained at day 30 and day 60 were similar than those observed at D15 for both groups (data not shown).

The inventors also explored whether the n-HA matrices compared to matrices without n-HA could interact with endogeneous osteogenic and angiogenic growth factors. They have tested two major growth factors that play a fundamental role in angiogenesis and osteogenesis, the isoform $VEGF_{165}$ and BMP2, an osteoinductive factor that could, by itself, induces mineralization and bone formation. Two days of implantation, corresponding to the inflammatory phase observed following material implantation, both samples retained the two growth factors but to a different extent. Strikingly, the amount of BMP2 retained on MATRI+ is 1.41 pg/µg protein extracted from the samples, while the matrix without n-HA retained only 0.12 pg/µg protein. For $VEGF_{165}$, the amount retained in MATRI+ and matrix without n-HA are 0.089 pg/µg protein and 0.055 pg/µg protein, respectively. With time of implantation, and during the formation of the dense mineralized tissue, the concentration of BMP2 (FIG. 8A) and $VEGF_{165}$ (FIG. 8B) decreased in both groups, compared to data obtained after 2 days, but remains significantly higher in the MATRI+ group after 30 and 60 days of implantation, compared to matrix without n-HA.

The scaffolds, matrices without n-HA (Group 1) and the composite scaffold MATRI+ containing n-HA (Group 2), were implanted in a critical size bone defect of 5 mm diameter and 6 mm depth in the femoral condyle of rats, for 15, 30 and 90 days. Micro-CT, quantification of mineralization (BMC and BMD analysis) and histological analysis were performed for both groups. As showed by micro-CT, matrices with n-HA (MATRI+) (FIG. 9A) formed within the bone defect, a highly dense mineralized tissue, compared to matrix without n-HA. Mineralization increases with time of implantation as shown by quantification analysis of the BMD and BMC (FIG. 9B) from day 15 to day 90 of implantation. BMC and BMD in the control group (empty) remain lower than in the other groups, whatever the time of implantation.

Histological data after 90 days of implantation confirmed, a high staining by von Kossa of the matrices with n-HA (MATRI+) compared with the matrix alone without n-HA or the empty group (FIG. 10A). Goldner staining evidenced a fibrous tissue in the empty bone defect, while bone formation was enhanced within the MATRI+ implant after 90 days of implantation and occurred in direct contact of the MATRI+ implant (FIG. 10B).

The invention claimed is:

1. A porous polysaccharide scaffold obtained by:
   i) preparing an alkaline aqueous solution comprising at least one polysaccharide, a cross-linking agent and a porogen agent,
   ii) transforming the solution into a hydrogel by placing said solution at a temperature from 4° C. to 80° C. for a sufficient time to allow cross-linking of said at least one polysaccharide,
   iii) submerging said hydrogel into a solvent, and
   iv) washing the porous polysaccharide scaffold obtained at step iii), wherein the alkaline aqueous solution of step i) further comprises hydroxyapatite and wherein the porous polysaccharide scaffold lacks exogenously added cells and growth factors.

2. The porous polysaccharide scaffold according to claim 1, wherein the porogen agent is selected from the group consisting of sodium chloride, calcium chloride, ammonium carbonate, ammonium bicarbonate, calcium carbonate, sodium carbonate, sodium bicarbonate and mixtures thereof.

3. The porous polysaccharide scaffold according to claim 1, wherein a weight ratio of the at least one polysaccharide to the porogen agent is in a range from 1:50 to 50:1.

4. The porous polysaccharide scaffold according to claim 1, wherein said at least one polysaccharide is selected from the group consisting of dextran, pullulan, agar, alginic acid, starch, hyaluronic acid, inulin, heparin, fucoidan, chitosan and mixtures thereof.

5. The porous polysaccharide scaffold according to claim 1, wherein said at least one polysaccharide is a mixture of pullulan/dextran in a ratio in a range from 95:5 to 5:95.

6. The porous polysaccharide scaffold according to claim 1, wherein said at least one polysaccharide is a mixture of pullulan/dextran/fucoidan in a ratio in a range from 70:20:10 to 50:20:30.

7. The porous polysaccharide scaffold according to claim 1, wherein said cross-linking agent is selected from the group consisting of trisodium trimetaphosphate (STMP), phosphorus oxychloride ($POCl_3$), epichlorohydrin, formaldehydes, carbodiimides, glutaraldehydes, and mixtures thereof.

8. The porous polysaccharide scaffold according to claim 1, wherein said hydroxyapatite is nano-hydroxyapatite.

9. The porous polysaccharide scaffold according to claim 8 wherein said nano-hydroxyapatite is obtained from a solution of phosphoric acid at a concentration between 0.3 to 1M, with a solution of calcium hydroxide at a concentration between 0.5 to 1.5M, through chemical precipitation at room temperature.

10. The porous polysaccharide scaffold according to claim 9, wherein said phosphoric acid concentration is 0.6M and said calcium hydroxide concentration is 1M.

11. The porous polysaccharide scaffold of claim 10, wherein said nano-hydroxide concentration is between 0.1 and 0.5% (w/v) or between 0.1 and 0.3% (w/v).

12. The porous polysaccharide scaffold according to claim 8 wherein a concentration of nano-hydroxyapatite in the alkaline aqueous solution is between 0.01 and 10% (w/v).

13. The porous polysaccharide scaffold according to claim 1, wherein said porous polysaccharide scaffold contains pores from 1 μm to 500 μm in size and the porosity is from 4% to 75%.

14. The porous polysaccharide scaffold of claim 13, wherein the pores are from 10 to 200 μm in size and the porosity is from 4% to 50%.

15. The porous polysaccharide scaffold according to claim 1 wherein said solvent is an aqueous solution.

16. The porous polysaccharide scaffold according to claim 1, wherein a weight ratio of the at least one polysaccharide to said porogen agent is in a range from 1:30 to 30:1 (w/w).

17. The porous polysaccharide scaffold according to claim 16, wherein said weight ratio is 75:25 (w/w).

18. The porous polysaccharide scaffold according to claim 16, wherein said ratio is selected from the group consisting of 70:20:10 (w/w), 50:30:20 (w/w), and 73:22:5 (w/w).

* * * * *